United States Patent [19]

Pablo Pivel Ranieri et al.

[11] Patent Number: 5,243,036
[45] Date of Patent: Sep. 7, 1993

[54] PROCESS FOR OBTAINING POLYMERS WITH ANTIVIRAL ACTIVITY

[75] Inventors: Juan Pablo Pivel Ranieri; Antonio F. Guerrero Gomez-Pamo; Luis Carrasco Llamas, all of Madrid; Ma Jesus Almel Armendariz, Tres Cantos; Juan Antonio Leal Ojeda, Madrid; Carmen Guerrero Benito, Segovia, all of Spain

[73] Assignee: Laboratorios Andromaco S.A., Madrid, Spain

[21] Appl. No.: 806,645

[22] Filed: Dec. 13, 1991

[30] Foreign Application Priority Data

Dec. 17, 1990 [ES] Spain ................................. 9003221

[51] Int. Cl.$^5$ ................................. C07G 3/00
[52] U.S. Cl. ................................. 536/4.1; 526/238.2; 526/238.23
[58] Field of Search ................. 536/4.1; 526/238.2, 526/238.23

[56] References Cited

U.S. PATENT DOCUMENTS

| | | | |
|---|---|---|---|
| 4,681,876 | 7/1987 | Marples et al. | 514/182 |
| 4,705,777 | 11/1987 | Lehrer et al. | 514/12 |
| 4,751,077 | 6/1988 | Bell et al. | 424/85.6 |

*Primary Examiner*—Nathan M. Nutter
*Attorney, Agent, or Firm*—Ladas & Parry

[57] ABSTRACT

A process for obtaining polymers with antiviral activity is disclosed. Molecules carrying carbonyl groups and hydroxyl groups in the $\alpha$ position relative to the carbonyl, and molecules carrying amino and sulfonated groups, react in water or in mixtures of water with water-miscible solvents. The reaction takes place under specific conditions of temperature, time and pH. The first reacting molecule may be a monosaccharide whereas the second reacting molecule may comprise aliphatic aminosulfates. Upon completion of the reaction the polymeric material is purified by conventional processes such that the polymeric material has a molecular weight between 1,500 and 100,000. The polymeric material has antiviral activity, either lacks or has very low toxicity and anticoagulant activity, and is thus suitable for pharmaceutical preparations for use in topical or systemic antiviral therapy in humans or animals.

15 Claims, No Drawings

PROCESS FOR OBTAINING POLYMERS WITH ANTIVIRAL ACTIVITY

DESCRIPTION

The present invention concerns a process for obtaining polymers by chemical reaction, under specific temperature, pH, and time conditions, between molecules carrying carbonyl and hydroxyl groups, with the latter in position α relative to the carbonyl, and molecules carrying amino and sulfonated groups, with the resulting polymers having antiviral activity, as a result of which they are suitable for use in the appropriate galenic form for application in human or veterinary medicine.

The antiviral activity, in vitro and in vivo in experimental animals, of specific sulfated polysaccharides and other sulfated polymers, such as agar, carrageenans, sulfated dextran, and sulfated polyvinyl are described. It has also been demonstrated that the distribution over a carbonated structure of groups sulfated with a specific spatial distribution produces compounds which present antiviral activity; however, to date, the activity of said compounds in vivo in dose and mode of application which can be used in humans has not been demonstrated (E. de Clercq, Trends in Pharmacol. Sci., 11, 198, 1990). The fundamental reasons for this lack of activity in vivo in humans could be predicted from the in vivo results obtained in experimental animals. In these, although antiviral activity was manifested, undesirable side effects such as increased coagulation time, toxicity, and inadequate bioavailability were also observed. Said effects are fundamentally associated with the anticoagulant properties of oligo/polysaccharides, with the large molecular size of the specimens used, and the presence of toxic contaminants.

Because of all this, various lines of investigation have been proposed which may be summarized as a search for sulfated oligomers derived from sulfated polymers which present antiviral activity without manifesting anticoagulant properties and whose bioavailability can be improved based on new galenic techniques.

Nevertheless, there is also the possibility that other carrier groups besides sulfate can provide antiviral activity to oligo/polymers when they are added to them in a specific order. Based on this, the study was proposed of which the results are reflected in the present invention by means of which are obtained by chemical reaction, under specific temperature, pH, and time conditions, between molecules carrying amino and sulfonated groups, polymers carrying sulfonated groups which, in addition to having antiviral activity, also present the advantages compared to the polysaccharides and other sulfated polymers that their anticoagulant activity is low or nonexistent, that they have a molecular weight sufficiently low to enable their transfer and absorption by appropriate galenic means, and that they are not toxic, nor are toxic compounds which could remain as contaminants used in obtaining them.

GENERAL DESCRIPTION OF THE PROCESS

Step 1: Preparation of the reaction mixture. In an appropriate container provided with a cover, is prepared the reaction mixture for dissolving the reacting molecules, one carrying carbonyl and hydroxyl groups and which is soluble in water or in water-miscible solvents, for example, a monosaccharide, such as glucose, mannose, galactose, etc., and the other carrying amino and sulfonated groups and which is soluble in water or in water-miscible solvents, for example, an aminosulfonic acid, such as taurine, cysteic acid, etc., in a quantity such that its concentration is between 1 mM and 2M and the molar ratio between amino groups and carbonyl groups is between 1:10 and 10:1. Said molecules are dissolved in an aqueous medium or a medium made up of mixtures of water-miscible solvent with water, buffered, with the pH adjusted by addition of acid or base such that the pH is between 1.0 and 9.0.

Step 2: Reaction. After the reacting molecules are dissolved in the appropriate medium, one proceeds to the condensation reaction. For this, the reaction mixture is heated to a temperature between 70° and 105° C., allowing it to react under moderate agitation no longer than the time sufficient for the concentration of the reacting molecule carrying the amino and sulfonated groups to become zero or to remain constant.

Step 3: Purification. The biochemically active polymeric material obtained as a result of the reaction described in the preceding step and which is soluble in the reaction mixture is purified by conventional processes such as gel filtration, ultrafiltration, or dialysis, etc., using appropriate strata or membranes and collecting the fractions whose molecular weight is between 1,500 and 100,000.

EXAMPLE 1

Preparation of the reaction mixture: Glucose is dissolved in 1 L of water to a final concentration between 3 and 12 mM in a 2-liter matrass provided with a teflon lid; between 0.1 and 0.3 L of a solution of cysteic acid in water, prepared to a final concentration of 40 to 60 mM and adjusted to a pH between 6.5 and 8.5 by adding sodium hydroxide is added. This is agitated until the two solutions are completely mixed.

Reaction: The reaction mixture is heated to 90° to 100° C. and held at this temperature under gentle agitation for a period of 3 to 5 days.

Purification: The solution resulting from the preceding step is concentrated by rotovapor at 40° to 50° C. to 1:5 to 1:10 of the original volume. It is dialyzed against water in a 3,000- and 10,000-dalton dialysis membrane for 48 hours. It is lyophilized. It is resuspended in water to a final concentration of 10 g L/1 and dialyzed against water in a 3,000- and 10,000-dalton dialysis membrane for 48 hours. It is lyophilized.

The product thus obtained is a polymeric material with a molecular weight between 3,000 and 50,000; its elemental composition is C 27 to 47%, H 3 to 7%, S 5 to 11%, N 2 to 6%, and O 32 to 58%, and it presents the following characteristics with regard to biological activity:

Said product is capable, under the conditions described below, of inhibiting the cytopathic effects of the Herpes Simplex 1 virus on He La cells "in vitro" at a concentration in the cellular culture between 10 and 150 μg mL/1. At said concentrations, said product does not present any toxicity of the He La cells. The conditions for the analysis of the antiviral effect, based on those described in B. Alarcon et al., Antiviral Res., 4, 231, 1984 and M. E. González et al., Antimic. Ag. Chemother., 31, 1388, 1987, are: Cells and virus: The Herpes Simplex type 1 virus (KOS) was grown in Vero cells, in Dulbecco Modified Eagle Medium (DMEM) supplemented with 10% fetal calf serum (FCS) and containing 10,000 IU of penicillin and 50 mg of streptomycin per ml. The concentration of the virus was estimated by plaque test on Vero cells. —Plaque test: The cells were serially grown in a single layer until confluence in plaques P60 and were incubated with 0.5 ml of 1:10 dilutions of the virus in phosphate-buffered saline (PBS) supplemented with 0.5% FCS. After an absorption period of 1 hour at 37° C., the inoculum was removed and an overlay of 5 ml of DMEM with 0.6% agar and 2% FCS was added. The single layers were incubated at 37° C. in humidified air containing 6% $CO_2$ for several days until the appearance of cytopathic effects. After these appeared, the overlay was removed, the single layer of cells was precipitated with trichloroacetic acid (TCA) to 5% and the lysis plaques were counted. Estimation of the cytopathic effect: Single layers of HeLa cells grown in DMEM were infected with HSV1 at a low rate of infection (0.0 to 0.4 plaque forming units (PFU)) in the presence of decreasing concentrations of product between 0 and 200 µg/ml. After 48 hours of incubation at 37° C., the cytopathic effects are studied in the cells, infected or not, by observation under a phase-contrast microscope.

Said product, injected intravenously in male SD rats at a dosage of 30 mg $kg^{-1}$ does not produce changes in coagulation time, conditions under which sodium heparinate totally prevents coagulation. Under said conditions, no external toxic manifestation is observed.

We claim:

1. A process for obtaining polymers with antiviral activity, comprising:
   preparing a reaction mixture of reacting molecules in a container having a cover, a first reacting molecule carrying a carbonyl group and an hydroxyl group, and a second reacting molecule carrying an amino group and a sulfonate group, the first and second reacting molecules being present in predetermined concentrations and dissolved in a medium such that both the first and second reacting molecules are soluble and the pH thereof is adjusted to lie within a predeteremined range;
   heating the reaction mixture and holding said mixture at a specific temperature under gentle agitation for a time sufficient to permit concentration of the second reacting molecule to decrease to a predetermined level; and
   purifying a product including sulfonated groups formed in the reaction mixture and collecting material with a molecular weight between 1,500 and 100,000.

2. A process as claimed in claim 1, wherein the product is purified by gel filtration, ultrafiltration or dialysis.

3. A process as claimed in claim 1, wherein the first reacting molecule contains a carbonyl (—CHO) and an hydroxyl group (—OH) in position α relative to the carbonyl group and is soluble in water or water-miscible solvents.

4. A process as claimed in claim 3, wherein the water-miscible solvents are selected from dimethyl sulfoxide, dimethylformamide, ethanol and methanol.

5. A process a claimed in claimed in claim 1 wherein the first reacting molecule comprises a monosaccharide selected from the evoup comprising glucose, galactose, mannose, xylose.

6. A process as claimed in claim 1, wherein the second reacting molecule contains a primary amino group (—$NH_2$) and sulfonate group (—$SO_3H$) soluble in water or water-miscible solvents.

7. A process as claimed in claim 6, wherein the second reacting molecule comprises an aminosulfonic acid selected from the group comprising taurine and cysteic acids.

8. A process as claimed in claim 1 wherein the concentrations of the first and second reacting molecule in the reaction mixture are between 1 mM and 2M.

9. A process as claimed in claimed in claim 1 wherein the concentration of the first and second reacting molecules in the reaction mixture are such that the molar ratio between amino groups and carbonyl groups is between 1:10 to 10:1.

10. A process as claimed in claim 1 wherein the pH of the reaction mixture is between 1.0 and 9.0.

11. A process as claimed in claim 1 wherein the reaction temperature is between 70° C. to 105° C., and maintained throughout the duration of the reaction so that variation in temperature is no greater than ±5° C. to 10° C.

12. A process as claimed in claim 1 wherein the temperature ranges between 90° C. to 105° C.

13. A process as claimed in claim 1 wherein the reaction time is sufficient for the second reacting molecule to react until its concentration is either constant or zero.

14. A process as claimed in claim 1 wherein the resultant polymeric material produced by the reaction is purified of the reagents using conventional biochemical processes such as gel filtration, ultrafiltration, dialysis, so that the molecular weight is between 1,500 and 100,000.

15. A process as claimed in claim 1 wherein the products obtained have antiviral activity, present low or non-existent toxicity and anticoagulant activity and are suitable for production of pharmaceutical preparations in galenic forms suitable for use in human and veterinary medicine.

* * * * *